United States Patent [19]

Sakurai et al.

[11] Patent Number: 4,875,170
[45] Date of Patent: Oct. 17, 1989

[54] METHOD AND APPARATUS FOR ESTIMATING LIFE EXPECTANCY OF MECHANICAL STRUCTURES

[75] Inventors: Shigeo Sakurai, Hitachi; Sadao Umezawa, Mito; Saburo Usami, Hitachi; Hiroshi Miyata, Mito; Hajime Toriya, Hitachi; Kuniyoshi Tsubouchi, Mito; Ryoichi Kaneko, Hitachi, all of Japan

[73] Assignee: Hitachi, Ltd., Tokyo, Japan

[21] Appl. No.: 206,924

[22] Filed: May 31, 1988

Related U.S. Application Data

[63] Continuation of Ser. No. 850,105, Apr. 10, 1986, abandoned.

[51] Int. Cl.$^4$ .................. G06F 15/20; G01M 7/00; G01N 21/16
[52] U.S. Cl. .................. 364/507; 364/551.02; 364/508; 356/237; 358/106; 340/679
[58] Field of Search .................. 364/506–508, 364/550, 551.02, 571.04, 571.05, 580; 340/679, 680; 356/237, 240; 358/106

[56] References Cited

U.S. PATENT DOCUMENTS

| | | | |
|---|---|---|---|
| 4,336,595 | 6/1982 | Adams et al. | 364/508 |
| 4,364,113 | 12/1982 | Sengebusch et al. | 364/507 |
| 4,484,081 | 11/1984 | Cornyn, Jr. et al. | 364/507 |
| 4,493,042 | 1/1985 | Shima et al. | 364/507 |
| 4,581,706 | 4/1986 | Kato et al. | 364/506 |
| 4,587,617 | 5/1986 | Barker et al. | 364/507 |
| 4,604,706 | 8/1986 | Fisher, Jr. et al. | 364/507 |
| 4,685,335 | 8/1987 | Sato et al. | 364/508 |
| 4,751,657 | 6/1988 | Imam et al. | 364/507 |

OTHER PUBLICATIONS

Feliss et al., Surface Analyzer, IBM Technical Disclosure Bulletin, vol. 25, No. 4, Sep. 1982, p. 2047.

Primary Examiner—Parshotam S. Lall
Assistant Examiner—Brian M. Mattson
Attorney, Agent, or Firm—Fay, Sharpe, Beall, Fagan, Minnich & McKee

[57] ABSTRACT

The life expectancy of a mechanical structure that undergoes repeated loading is estimated by determining the maximum crack length on the surface of the structure. The maximum length of the cracks on the surface of the structure is related to the life ratio of the structure, wherein the life ratio is a ratio of the number of loads the structure has undergone to the number of loads the structure will undergo until failure. An optical system is used to measure the crack length of the cracks on the surface of the structure being inspected. A statistical distribution of greatest length cracks for a sampling of areas within a larger area can be made. Apparatus is provided to statistically process such distribution data to obtain a statistically estimated maximum length crack for the larger area. The maximum crack length determination can be used to estimate the life expectancy of the structure from the relationship between crack length and life ratio.

13 Claims, 13 Drawing Sheets

METHOD AND APPARATUS FOR ESTIMATING LIFE EXPECTANCY OF MECHANICAL STRUCTURES

This application is a continuation of application Ser. No. 850,105, filed 4/10/86, now abandoned.

BACKGROUND OF THE INVENTION

1. FIELD OF THE INVENTION

This invention relates to a method and apparatus for estimating the life expectancy of mechanical structures to which a repeated load is applied, and more particularly it is concerned with a method and apparatus for estimating the life expectancy of mechanical structures to which a repeated or fluctuating load is applied in a high temperature atmosphere.

2. DESCRIPTION OF THE PRIOR ART

Mechanical structures which are subjected to a repeated load in a high temperature atmosphere include, inter alia, turbines of electric power plants. In a turbine of an electric power plant, structural members of a turbine suffer damage due to thermal fatigue and creep, when the turbine is started and shut down repeatedly or the load applied thereto undergoes fluctuations. The result of this would be that the structural members might develop crack formation due to accumulated damage caused by the fatigue and creep, thereby causing a reduction to occur in the strength of the structure. In this case, there would be the risk that, unless an estimation was made of the life expectancy of the structure from the standpoint of its strength, rupture of equipment might occur and cause an accident on a large scale to take place in the electric power plant. In this connection, it is of particular importance that estimation of the life expectancy of the turbine casing, rotor and various types of valves be made from the standpoint of their strength.

Heretofore, it has been the usual practice, in designing this type of equipment, to set a high factor of safety based on the creep strength of the material used, thereby increasing reliability. Thus, estimation has rarely been made of the life expectancy of the equipment of the electric power plant. As it now stands, however, about one half the oil-burning electric power plants now in operation have passed the limit of their designed useful life, and the time has come to determine whether they can be left in service or replaced. Thus, it is now earnestly desired that a reliable method of estimating the life expectancy of mechanical structures be established.

Meanwhile, a change in demand for electric power has made it necessary to operate electric power plants, which were designed to meet the requirement of a base load, in such a manner as to start and shut down to cope with changes in load. When the operating conditions become severe, it is presumed that the useful life of the electric power plants naturally becomes short. Thus, it is quite important to estimate the life expectancy of such plants.

If it is possible to determine by non-destructive tests the damage suffered by the turbine casing, main valve and regulating valves to enable the life expectancy to be estimated, the reliability of a plant would be greatly improved. However, no proposals have ever been made to provide a method or an apparatus which would admirably suit this purpose.

With regard to the turbine rotor, however, system proposals have been made, as disclosed in Japanese Patent Examined Publication Nos. 21169/80 and 25842/83, for example, to sense the temperature of steam and gas in the vicinity of the rotor and the temperature on the inner surface of the casing. Based on the values of the sensed temperatures the system calculates 12 thermal stresses which would be applied to the rotor and controls the operation of the turbine based on the rate of change and the absolute value of the thermal stresses, to thereby avoid the development of excessively high thermal strain in the rotor.

The system referred to hereinabove is intended to avoid the development of excessively high thermal strain in the turbine rotor and to prevent the service life of the rotor from becoming shorter than its designed useful life, and is unable to estimate the life expectancy of the rotor. Particularly, in those plants which have been operated under severe conditions, it is impossible for this system to estimate the life expectancy of the rotor therein.

As a code for estimating the life expectancy of a steam turbine rotor, "SAFER" is known which is based on linear destruction dynamics (Research Report No. 283021, reported by Electric Power Central Research Institute, December 1983).

An electrochemical method has been applied to the art of non-destructive diagnosis of deterioration with respect to time in steam turbines as reported in On-the-Site Technology of Electricity, Vol. 23, No. 261.

The problem with these proposals of the prior art is that, although they may produce results which are somewhat reliable under a certain condition, they produce conflicting results and are misleading under other conditions.

SUMMARY OF THE INVENTION

Object of the Invention

This invention has as its object the provision of a method and apparatus for estimating non-detructively and with a high degree of accuracy the life expectancy of mechanical structures which are subjected to a repeated load or a fluctuating load.

Statement of the Invention

This invention is based on the discovery that, in a structure subjected to a repeated load in a high temperature atmosphere tending to develop creep, minuscule or micro cracks are formed on the surface of the structure at initial stages of its service and their development is closely related to the useful life of the structure.

The outstanding characteristics of the invention are that the life expectancy of a structure is estimated based on the maximum length of the cracks formed on the surface of the structure. Preferably, the maximum length of the cracks found on the surface of the structure is obtained by a statistical process from the maximum lengths of the cracks on sampling surfaces of limited areas.

DESCRIPTION OF THE PREFERRED EMBODIMENTS

Before describing in detail the preferred embodiments of the invention, the principles on which the method according to the invention of estimating the life expectancy is based will be described.

Figure 1:
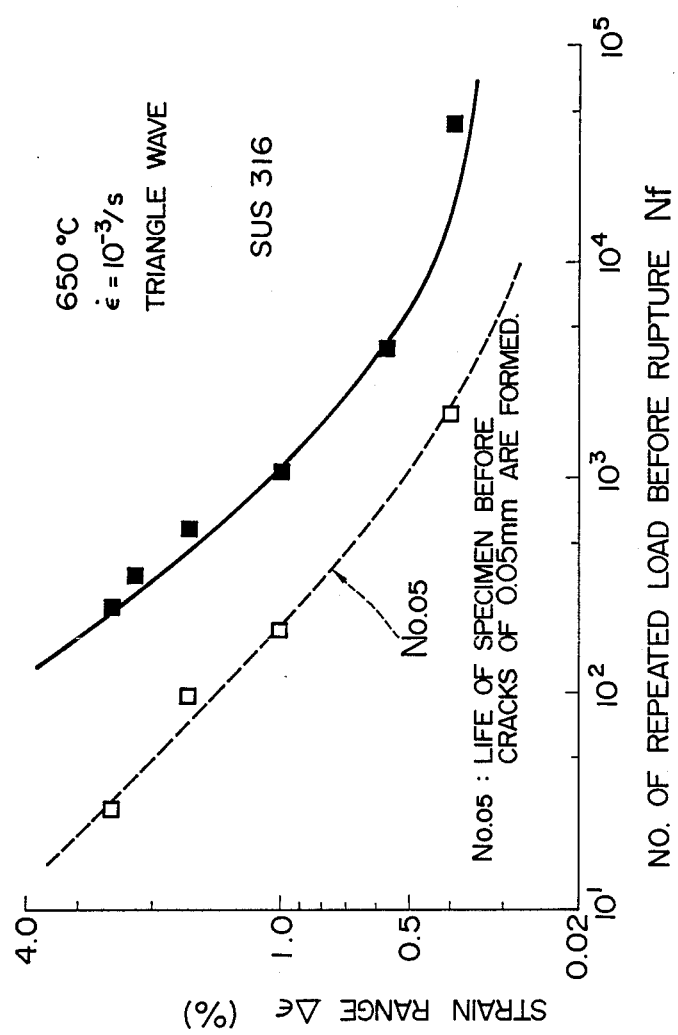
FIG. 1 is a diagram showing the number of times a repeated load is applied to the specimens until they rupture and the number of times a repeated load is applied to the specimens until minuscule cracks are formed on their surface.

FIG. 1 is a diagram showing the number of times a repeated load was applied to smooth specimens, in an atmosphere of 650° C., of austenitic stainless steel (SUS316) used for forming a main steam pipe of a steam turbine and other parts until crack formation occurred, and the number of times a repeated load was applied thereto until rupture occurred. In this case, the strain speed $\epsilon$ was $10^{-3}$/sec and the waveform of a load for causing strain to occur was triangular so that the strain was simply allowed to increase at the aforesaid strain speed and was simply allowed to decrease when a predetermined strain range $\Delta\epsilon$ was reached. In the figure, a white square represents the number of repeated load that has caused the greatest crack formed at the surface of each specimen to reach 0.05 mm in size, and a black square indicates the number of repeated load that has caused rupture to occur in each specimen.

This shows that, when the strain range at $\Delta\epsilon$ was 1%, a crack of 0.05 mm in size was formed at the surface as the number of repeated load $N_f$ reached about 200, and rupture occurred as the number of repeated load $N_f$ reached 1000.

As can be clearly seen in FIG. 1, a crack of 0.05 mm in size was invariably formed when the number of repeated load was 10 to 20% of that which caused rupture to occur, no matter what the value of the strain range $\Delta\epsilon$ might be. Stated differently, this would show that if the application of repeated load is continued when a minuscule or micro crack of about 0.05 mm in size is formed, rupture would occur when the number of repeated load becomes five to ten times as great as the number of repeated load that has caused the formation of the minuscule or micro crack to occur.

This would show that the formation and progress of minuscule or micro cracks is an important factor in determining the life of a specimen until rupture occurs. Thus, the accuracy with which estimation of the remainder of useful life is made could be greatly increased if the process of the formation and progress of cracks could be quantitatively analyzed.

Figure 2:
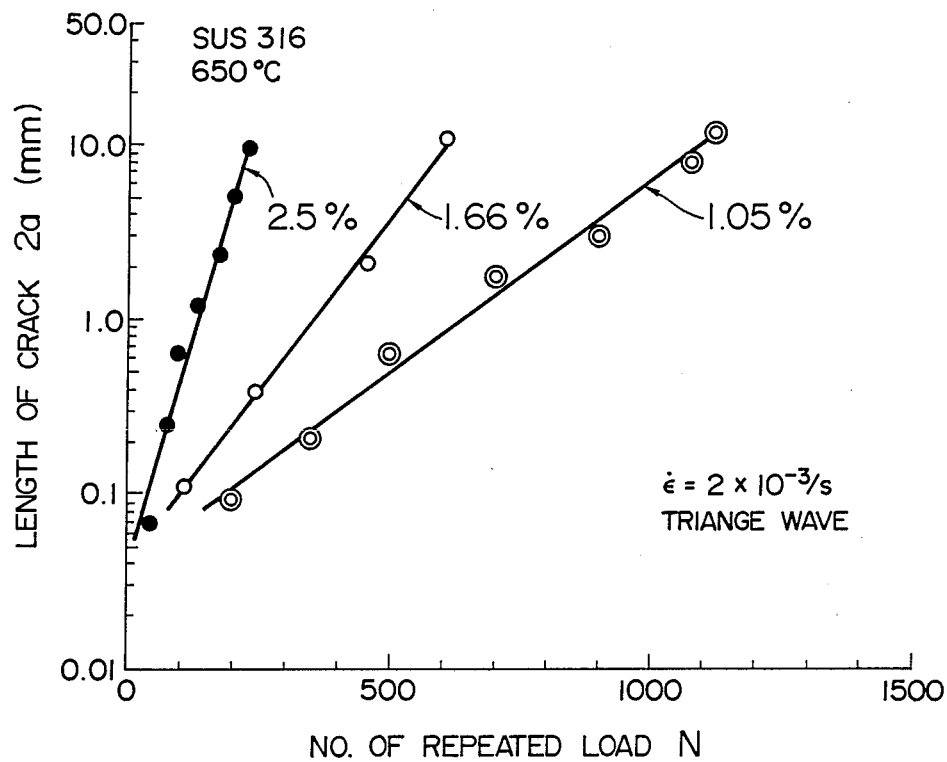
FIGS. 2 and 3 are diagrams showing the progress of cracks.

FIG. 2 shows the progress of minuscule or micro cracks by using the strain range $\Delta\epsilon$ as a parameter. The specimens used were of stainless steel (SUS316), the strain speed $\epsilon$ was $2\times10^{-3}$/sec and the waveform of the load was triangular.

In the graph shown in FIG. 2, the ordinate represents the length of cracks formed on the surface of the specimens which is shown on a logarithmic scale, and the abscissa indicates the number of repeated load. As can be seen in the figure, the process of progress can be indicated approximately linearly for the overall deformation range. Stated differently, this shows that the logarithm of the length of cracks is linearly related to the number of repeated load.

Figure 3:
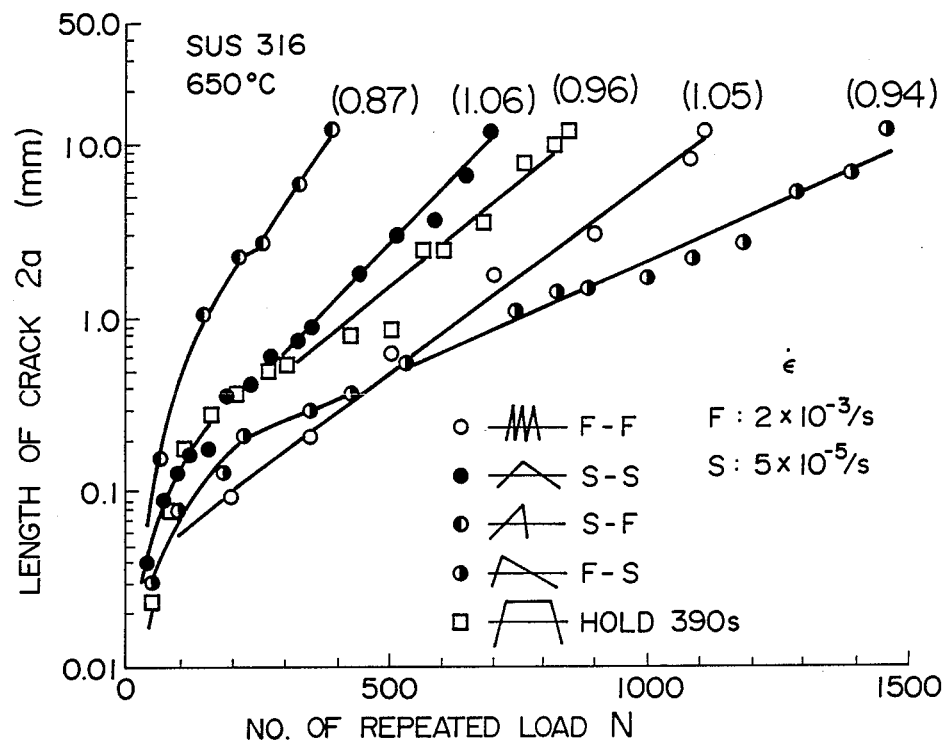

Useful life is an atmosphere of high temperature may depend to a great extent on the strain speed and the waveform of load. FIG. 3 shows the manner of progress of cracks with respect to various waveforms of load. FIG. 3 shows the results of experiments conducted by using five waveforms of load or F-F, S-S, S-F, F-S and Hold 390 sec. These waveforms are explained in detail as follows:

(i) F-F . . . A load was applied at a strain speed $\dot\epsilon=2\times10^{-3}$/sec in one direction and the same load was applied at the same speed in an opposite direction.

(ii) S-S . . . A load was applied at a strain speed $\dot\epsilon=5\times10^{-5}$/sec in one direction and the same load was applied at the same speed in an opposite direction.

(iii) S-F . . . A load was applied in a positive direction at a strain speed $\epsilon=2\times10^{-3}$/sec and in an opposite direction at a strain speed $\dot\epsilon=3\times10^{-5}$/sec.

(iv) F-S . . . This waveform is reversed to the waveform shown in paragraph (iii).

(v) Hold 390 sec . . . A load is applied in stepped fashion for 390 seconds and then the same load is applied in an opposite direction. As the results of the experiments shown in FIG. 3 indicate, the life of the specimens (unitl rupture occurs) may greatly depend on the manner of progress of the minuscule or micro cracks formed under all the waveforms of load including Hold 390 sec in which it has generally been believed that creep damage is marked and F-F, S-S, F-S and S-F which are each a serrated waveform. Even in the specimens that have suffered damage in such a manner that fatigue and creep coexist, the logarithm of twice the length of the cracks (2a) and the number of repeated load N can be approximated substantially linearly. The following relation holds between them:

$$\log 2a = C \cdot N \ldots \quad (1)$$

Thus, the crack progress speed $da/dN$ can be expressed as follows:

$$\frac{da}{dN} = C \cdot a$$

Assume that, in equation (2) showing the progress of minuscule or micro cracks, a crack has an initial length of 50 μm which is the diameter of a grain of crystal, and a final length of 10 mm which is the length that has caused a rupture in the specimen. Then, the following equation can be obtained from equation (2):

$$\int_{0.05}^{10} \frac{1}{d} \, da = C \cdot \int_{N_o}^{N_f} dN \quad (3)$$

Thus, the following equation can be led from equation (3):

$$C = \frac{2 \cdot 3}{N_f - N_o} \quad (4)$$

$N_o$ is a crack formation life (the number of repeated loads applied before a crack of the initial length of 50 $\mu$m is formed) which represents an initial stage of the total life before rupture occurs. Therefore, the early stage can be neglected and $N_o$ can be considered 0 (zero). This assumption is logical because cracks of several scores of $\mu$m are usually present at the surface of structural members of machines before they are put to use as the result of machining or the surface being coarse.

By substituting equation (4) into equation (1), the following equation can be obtained:

$$\log 2a = 2 \cdot 3 \times \frac{N}{N_f} + C' \quad (5)$$

Thus, it is shown that, if the length of the cracks can be determined, the life ratio $N/N_f$ or the life expectancy can be estimated. However, if the influence of $C'$ is great, then there is a risk that great errors could be made with the life expectancy that is estimated.

Figure 4:
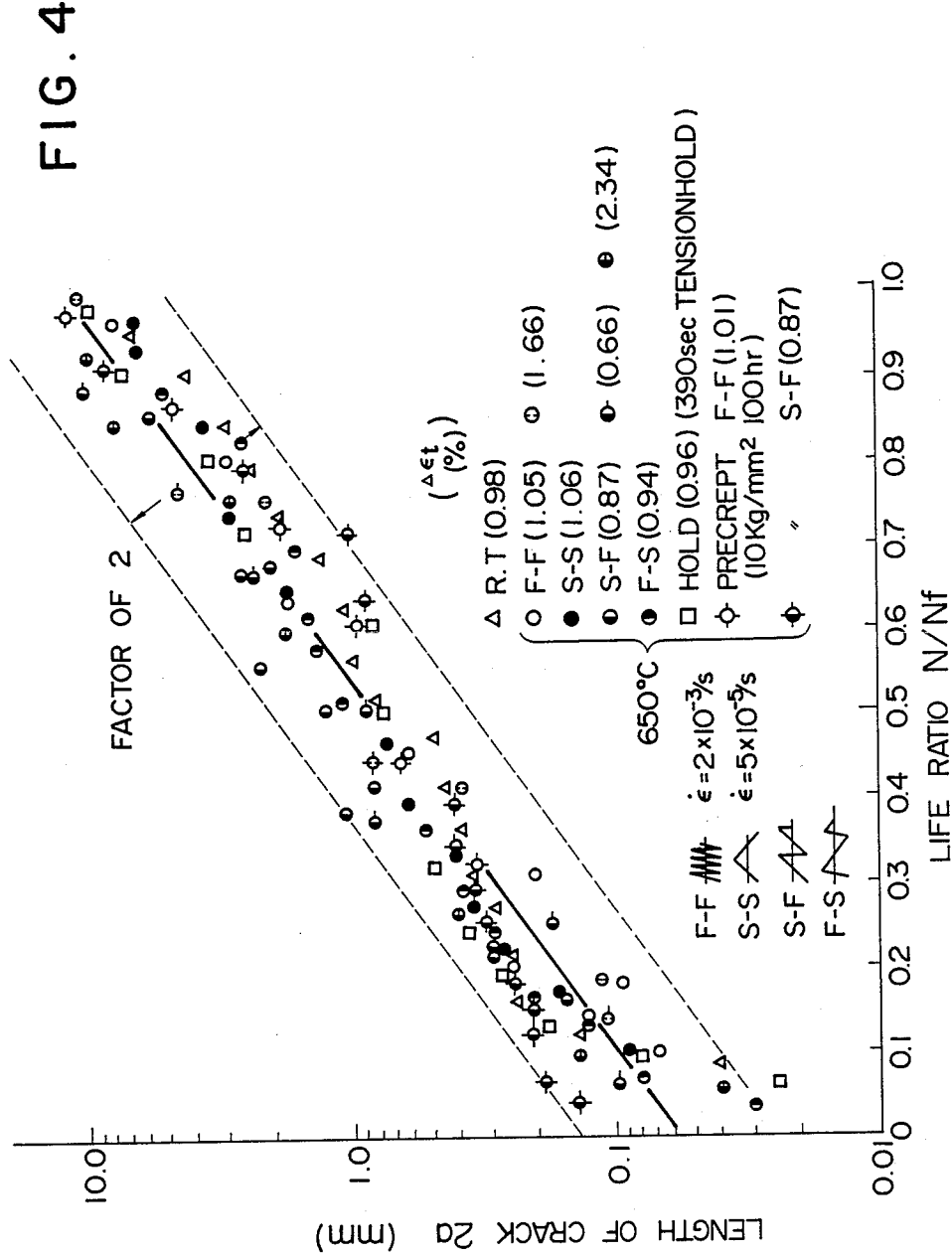
FIG. 4 is a diagram showing the relation between the length of cracks and the life ratio.
Figure 6:
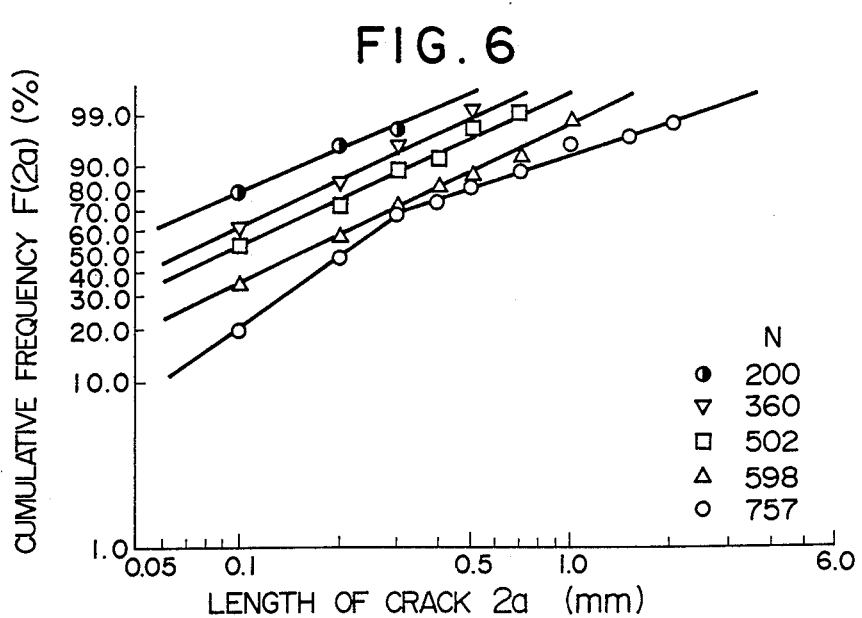
FIGS. 6 and 7 are diagrams showing the relation between cumulative frequency and the length of cracks.

Thus, attempts were made to actually measure the life ratio in relation to the progress of cracks under various conditions. The results obtained are shown in FIG. 4, in which like marks indicate matters similar to those indicated in FIG. 3 and the strain range of each case is shown in brackets. In FIG. 6, RT indicates that strain was caused by applying a load of the waveform F-F at room temperature, and Precrept (10 kg/mm², 100 hr) shows that specimens used had creep produced beforehand under a condition shown in brackets.

The results of the experiments show that, in spite of variations in the conditions for applying a load, the relation between log 2 a and $N/N_f$ is linear in the range of variation of a factor of 2.

Figure 5:
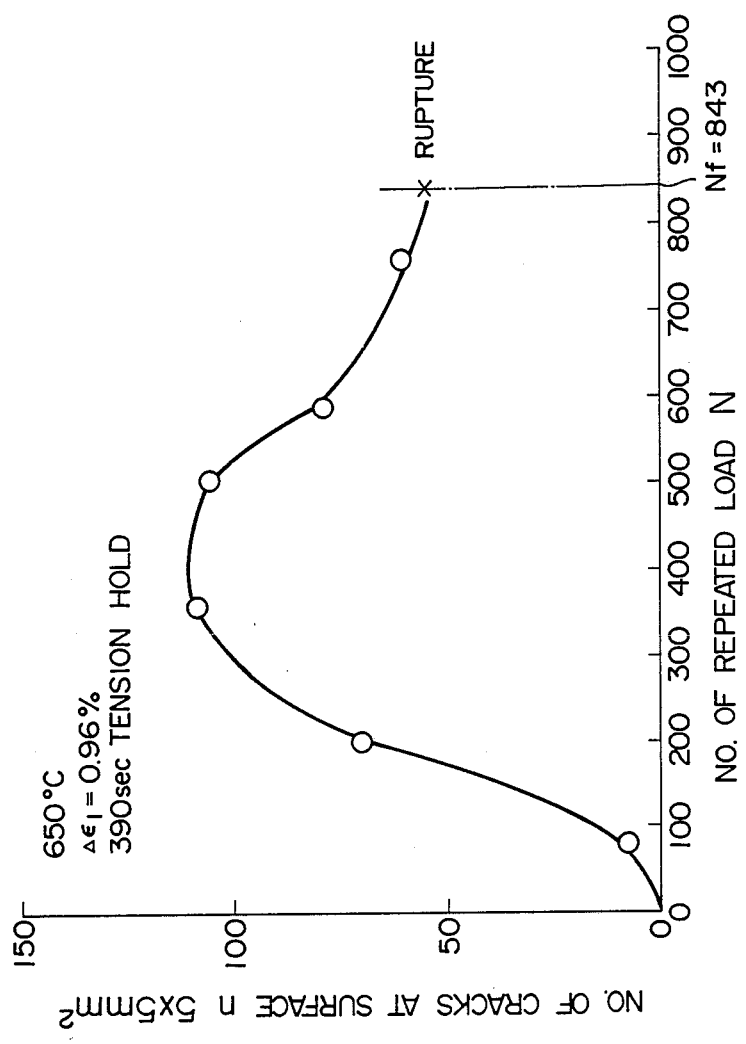
FIG. 5 is a diagram showing the relation between the number of cracks on the surface and the number of times a repeated load is applied to the surface.

This finding forms the basis of the method of estimating the life expectancy according to the invention. The length of cracks shown in FIG. 4 represents the behaviour of progress of the main crack or the crack which causes rupture to occur in a specimen. In actual practice, however, a multiplicity of minuscule or micro cracks would be formed at the surface of a structural member and grow in size or combine with each other into large cracks until rupture results. FIG. 5 shows a change in the number of cracks formed in a specific area (5×5 mm²) of the surface of a specimen. In the figure, it will be seen that cracks are formed separately and their number increases until the number of repeated loads reaches 400. However, after the number of repeated loads has passed this level, the cracks are combined with each other and grow in size while the number of cracks in the specific area tends to decrease. The behavior of the group of these minuscule or micro cracks would be directly responsible for the progress of actual damage. Thus, in order to estimate the life expectancy based on the relation between the lengths of cracks and the life ratio shown in FIG. 4 by handling the group of minuscule or micro cracks statistically, a process of establishing the length of the greatest crack of all the cracks of varying lengths was introduced.

In order to confirm that it is possible to handle the distribution of the lengths of cracks from the standpoint of mathematical statistics, experiments were conducted on subjecting the lengths of cracks to Welbull plotting, as shown in FIG. 6. As can be seen in the figure, the lengths of cracks can be approximated by Welbull distribution. The strength of a mechanical structure can be decided by the length of a crack of the greatest size of all the cracks in the distribution. Thus, when one defines as the main crack a crack of the greater size in the group of minuscule or micro cracks that has been detected, one could consider the size of the main crack as a parameter of the degree of damage which the structure has suffered at that particular point in time. Therefore, when the actual degree of damage suffered by equipment was determined, an extreme value statistical process was used for estimating the length of the greatest crack in a zone to be inspected from the distribution of cracks formed at sampling surfaces of the equipment.

More specifically, the distribution of the maximum value was determined in accordance with Gumbel distribution which is a double exponent type distribution expressed by the following formula:

$$F_x(X) = \exp\left[-\exp\left(-\frac{x - \lambda}{\alpha}\right)\right] \quad (6)$$

where
X: length of the greatest crack in one sample as a variable of extreme value.
$\lambda$: position parameter.
$\alpha$: measuring parameter.

Figure 7:
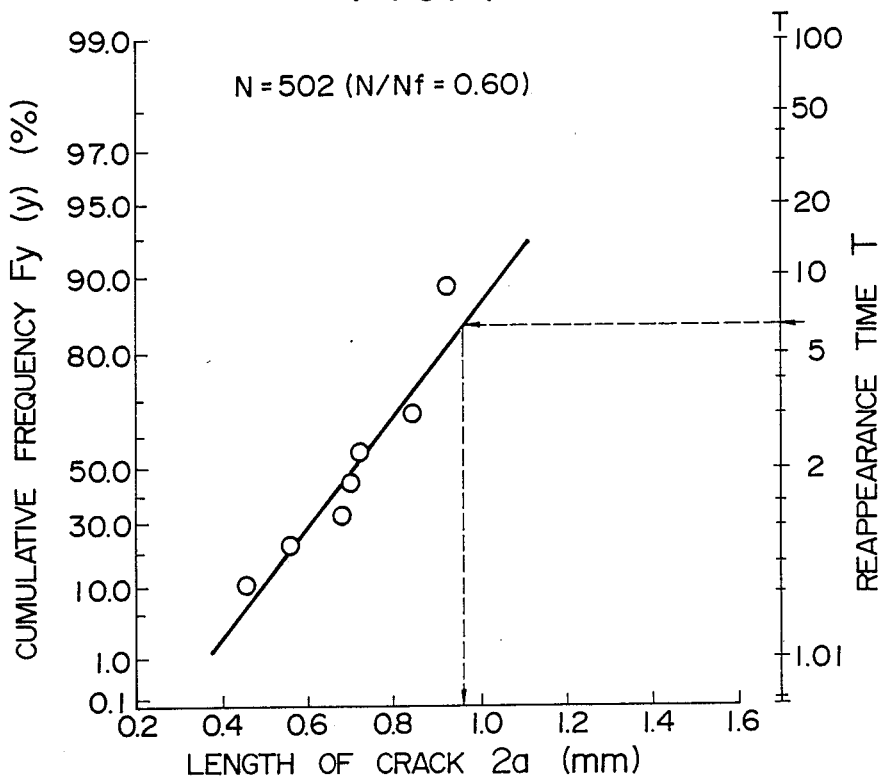

As a process for determining the parameters of $\lambda$ and $\alpha$, an extreme value calculation process can be used in which linear unbiased estimates are used from sample data. As a graphic calculation process, a process using probability paper can be used. In these experiments, the process using probability paper was used. The results are shown in FIG. 7 which shows extreme values statistical paper wherein the ordinate represents cumulative frequency F, (y) and the abscissa indicates the length of the crack 2a in an arithmetic scale. The ordinate on the right side of the figure represents what is referred to as a reappearance time T used for estimating the length of the greatest crack in the zone to be inspected. T is given as the ratio of the area of one sampling to the zone of equipment to be inspected.

Figure 8:
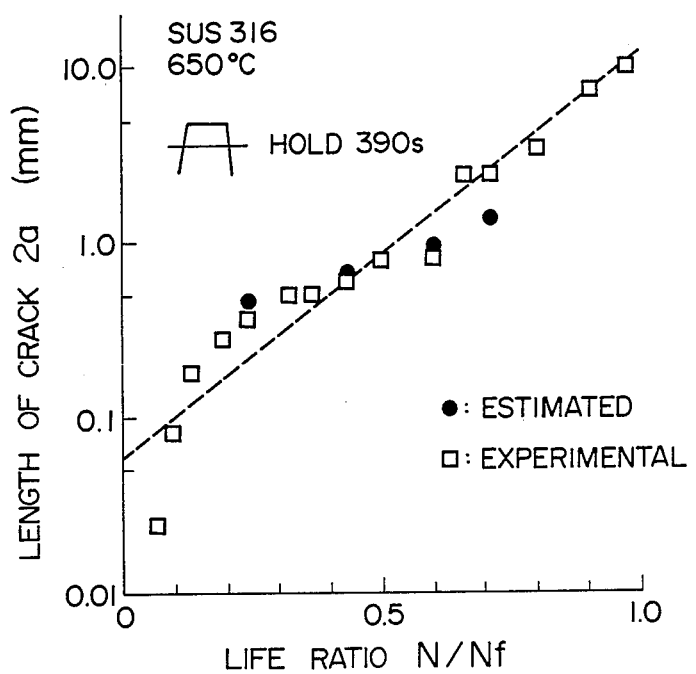
FIG. 8 is a diagram showing the length of cracks in relation to the life ratio.

FIG. 8 shows the results of comparison of the value of the length of the greatest crack estimated by the process described hereinabove with the value of the length of the greatest crack actually measured. In FIG. 8, a black circle represents a life ratio obtained from the estimate of the length of the greatest crack, and a white square indicates a life ratio obtained from the length of the greatest crack detected in the entire surface of the zone to be inspected. It will be seen that the estimate matches the measurement.

Thus, it has been confirmed that the process of estimating the length of the greatest crack by applying an extreme value statistical process to the distribution of minuscule or micro cracks is very high in accuracy, and that the life expectancy can be estimated from the estimate of the length of the greatest crack obtained by this process based on the relation between the lengths of cracks and the life ratio described hereinabove and shown in FIG. 4.

The length of a crack that would cause rupture to occur has been described as being 10 mm. However, it is not in all the structures that rupture would occur when the length of a crack has reached this level, and some structures might be able to have a longer useful life even if this level is exceeded, depending on the type of the structure. Thus, in estimating the life expectancy by the method according to the invention, lengths of cracks indicating the limit of the useful life of structures of different types are determined beforehand.

The number of repeated load $N_f$ applied before the size of a crack reaches a critical value for the useful life before rupture occurs may vary depending on the quality and strength of material. Thus, if the value of $N_f$ is obtained in a certain strain range by using specimens of the same material and the life ratio $(N/N_f)$-crack length characteristic shown in FIG. 4 is obtained beforehand, then it is possible to obtain the current life ratio of a structure based on the length of the greatest crack.

Apparatus suitable for carrying the aforesaid method of estimation into practice will now be described. In this case, the object of estimation selected is a casing of a steam turbine.

Figure 9:
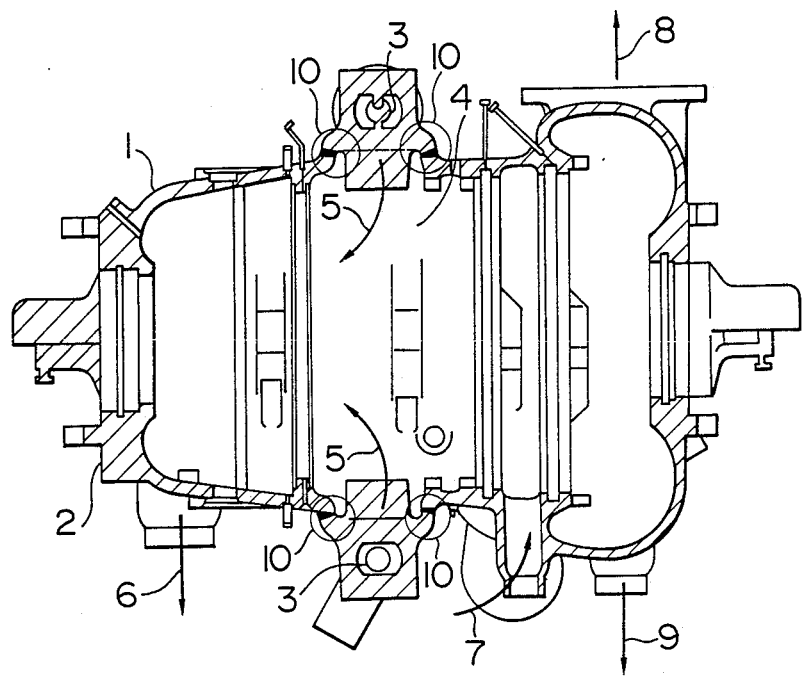
FIG. 9 is a sectional view of a turbine casing.

FIG. 9 shows a turbine casing of a high pressure stage of a steam turbine which is composed, as shown in the figure, of an upper casing member 1 and a lower casing member 2. Main steam 5 of high temperature and pressure flows axially in the casing after passing through a regulating valve chamber 3, and flows as exhausted steam 6 of high pressure into a regenerator, not shown, where it is heated to a high temperature and pressure level and introduced as reheated steam 7 into an intermediate stage. After flowing through the intermediate stage, the major proportion of the reheated steam 7 enters a low stage as exhausted steam of medium pressure and the rest is released from the casing as extracted steam 9.

This type of casing is a exposed to steam of high temperature and pressure. The steam causes thermal stresses of high magnitude to be applied when the steam turbine is started and shut down by a sudden variation in temperature from one layer to another of the structure. Thus, the casing is subjected, at the same time, to fatigue damage caused by repeated application of thermal stresses at startup and shutdown and creep damage due to prolonged application of load or internal pressure in a high temperature atmosphere.

In the method according to the invention, microscopic damage on the surface of a member of a structure of high temperature subjected to creep and fatigue is detected, and the degree of damage is determined. The life expectancy of the structure is estimated on the data collected by the damage detection. When the invention is applied to the steam turbine casing referred to hereinabove, the object to be inspected is limited to a zone of the casing which is assumed to be exposed to the greatest damage. Selection of the zone may be effected by determining the position in which the greatest stress is applied to the casing as a result of the analysis of the stress applied to the casing as a whole or by taking into consideration the results of studies carried out in the past. Once the zone to be inspected is selected, damage is determined in several zone positions which are selected by sampling. In this embodiment, an inlet portion of a main steam pipe, which is subjected to excessively large stresses, is selected as the zone to be inspected.

Figure 10:
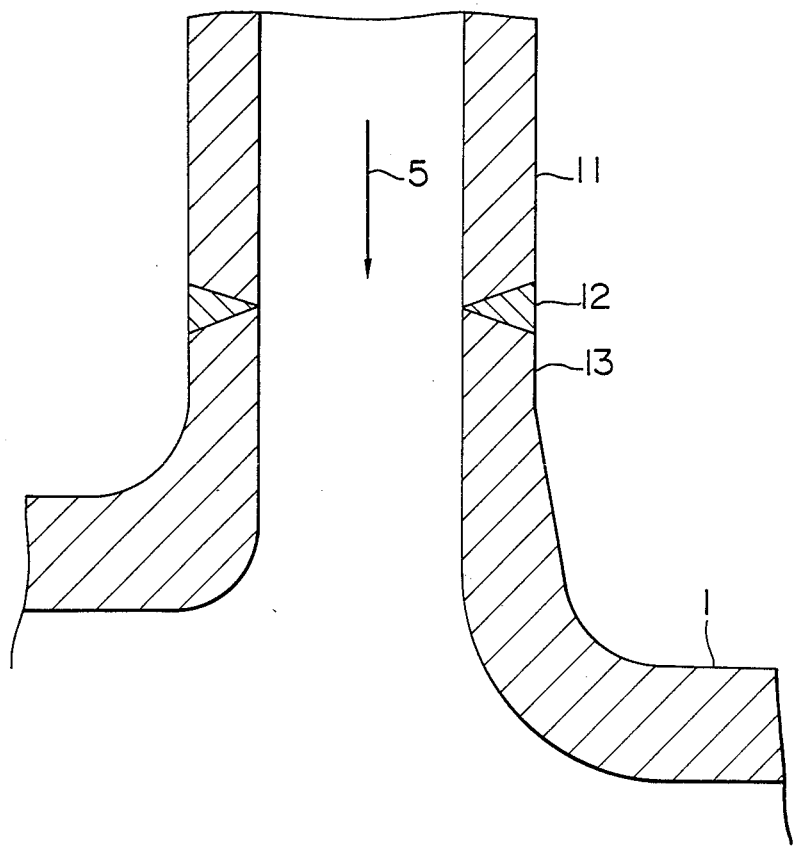
FIG. 10 is a detailed view of a portion of the main steam pipe.
Figure 11:
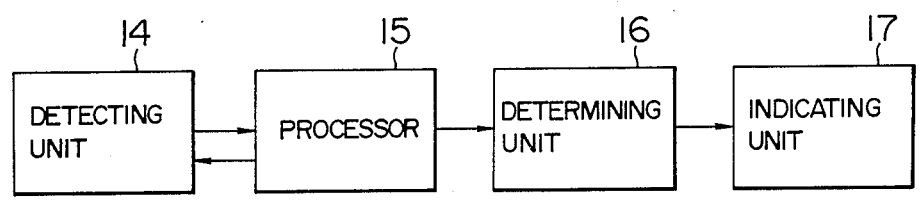
FIG. 11 is a block diagram of the basic construction of the apparatus according to the invention.
Figure 12:
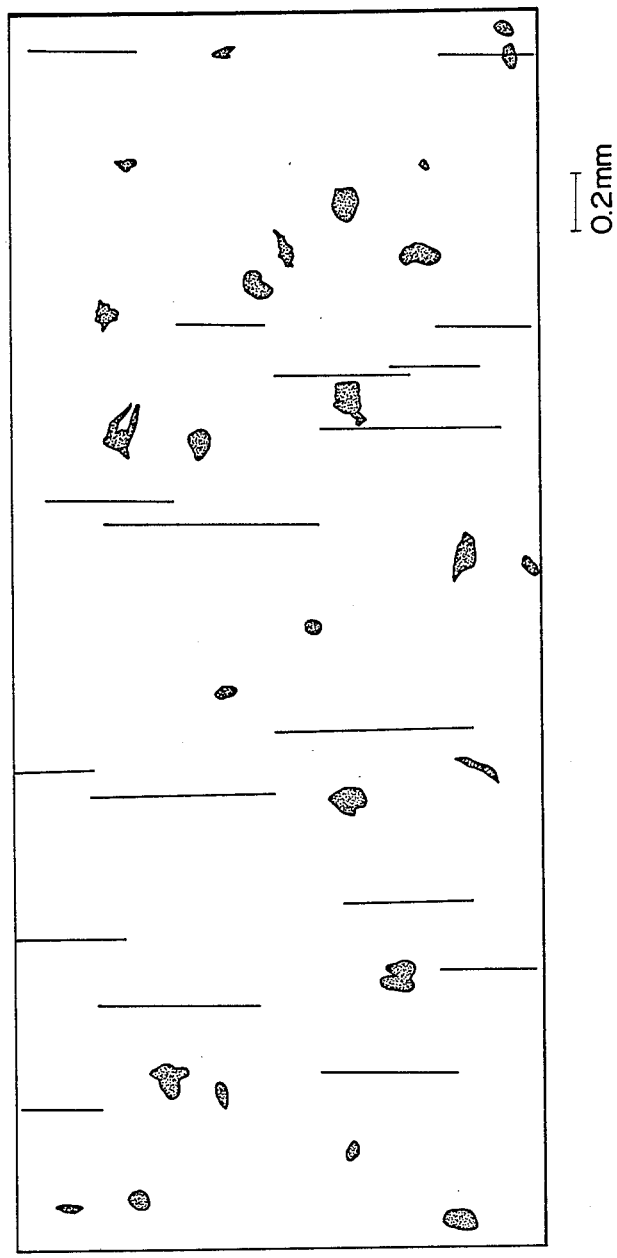
FIG. 12 is a view showing the distribution of cracks on the surface of the objects of estimation.

FIG. 10 shows an inlet portion of a main steam pipe 11 which is joined to the casing 1 of a steam turbine by a weld 12 which is exposed to the steam 5 of high temperature and pressure. Thermal stress is repeatedly applied to the weld 12 at turbine startup and shutdown due to a variation in temperature from one layer to another in the thickness direction. Particularly, a zone 13 adjacent the weld 12 tends to be subjected to stress concentration because the material and structure become discontinuous at this zone. Thus, an excessively large load is repeatedly applied to the zone 13, so that creep and fatigue damage suffered by the zone 13 is considered to be greater than that suffered by other zones. The basic construction of the apparatus according to the invention suitable for carrying out the method of estimating the life expectancy will be described by referring to FIG. 11. The numeral 14 designates a detecting unit for detecting the distribution of minuscule or micro cracks ranging from several $\mu$m to several mm formed at the surface of the zone 13 to be inspected. The detecting unit 14 has the function of performing random sampling in a predetermined area of the zone to be inspected. FIG. 12 shows one example of the distribution of minuscule or micro cracks which was obtained by studying the surface of the area at initial stages of its useful life at which it is subjected to creep and fatigue damage at 650° C. The numeral 15 designates a processor for detecting an extreme value of the lengths of cracks in one distribution of minuscule cracks in the samplings that are inputted to the processor 15; and for estimating, based on the extreme values of several samplings by the extreme value statistical process, the length of the greatest crack existing in the zone to be inspected. This zone is several to several scores of times as large as the area in which random sampling has been performed. The software used for working the processor 15 may include a program for estimating a parameter of the statistical distribution of extreme values by using a linear unbiased estimating process. The processor 15 also has the function of performing an $x^2$ test or Kolmogorov-Smirnov test on sampling data from the statistical standpoint to perform an appropriateness test by which it is determined whether the sampling data under study can be taken to represent a sample of a certain distribution, to thereby determine the appropriateness of the number of data and samplings. When the result of the appropriateness test is negative, the processor 15 performs a feedback operation to perform sampling again by the detecting unit 14. When the number of data and samplings have been determined to be appropriate, the processor 15 produces an estimation which is inputted to a determining unit 16 which estimates the degree of damage and calculates the life expectancy which is outputted to an indicating unit 17. Unit 17 indicates the estimated length of the greatest crack, its variance value and the life expectancy based thereon.

Figure 13:
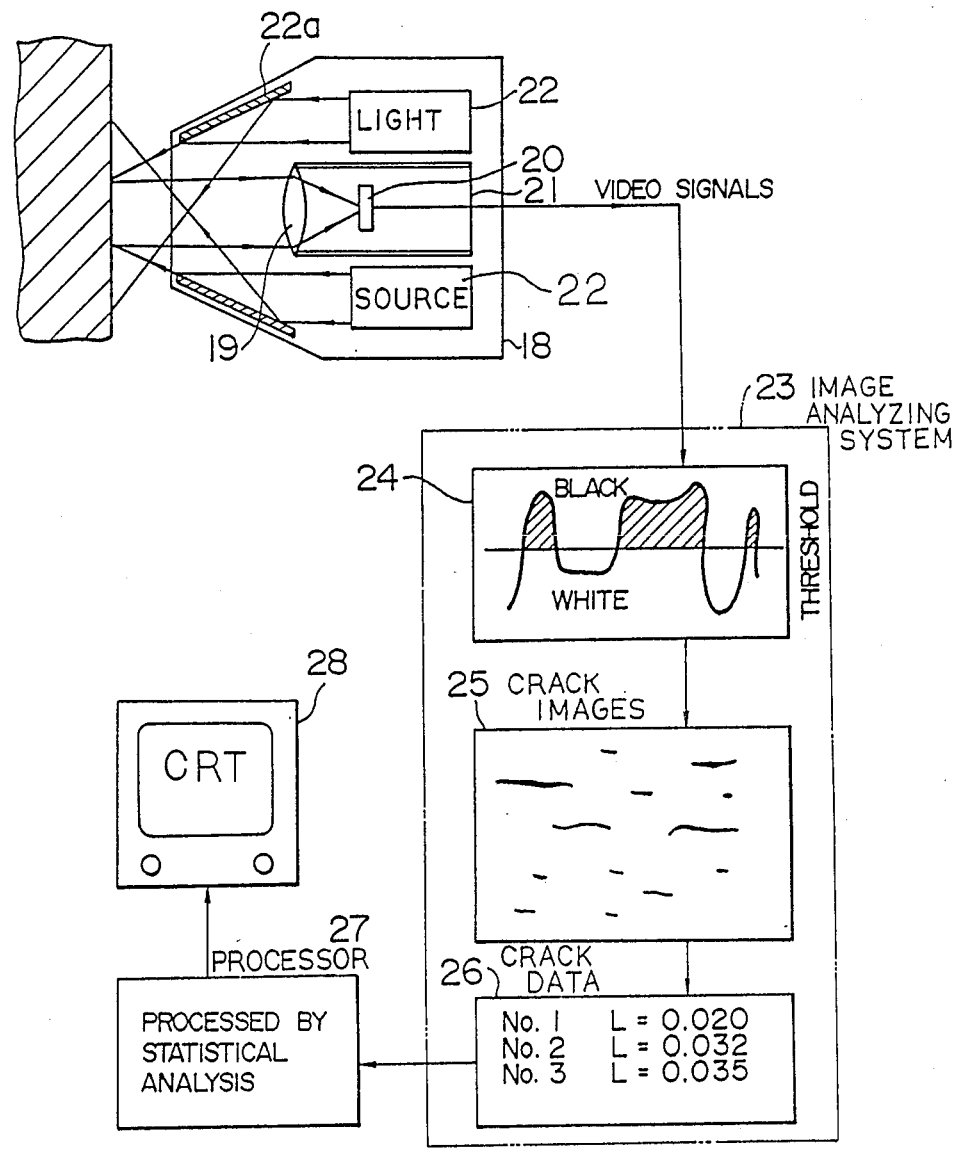
FIG. 13 is a view of the apparatus comprising one embodiment of the invention.

FIG. 13 shows one embodiment of the apparatus suitable for carrying into practice the method of estimating the life expectancy according to the invention, which uses a TV camera having a magnifying lens system as detecting means for detecting cracks on the surface of the weld of the main steam pipe. The detecting means 18 comprises a compact industrial television camera 21 including a magnifying lens 19 capable of altering magnification between 20 and 200 X, and an image sensor 20 of high sensitivity, such as a solid state image forming element, capable of sensing an inputted field of view and converting optical images into video signals. The television camera 21 is located in a central portion of the detecting means 18, and a light source 22 is arranged around the image sensor 20. Light source 22 emits light rays which are reflected by a mirror 22a located in a lower portion of a head of the detecting means 18 to illuminate at an angle of about 45 degrees the surface of a portion of the weld to be inspected. This facilitates the detection of minuscule or micro cracks. Video signals are inputted from the detecting means 18 of the aforesaid construction to an image analyzing system 23 where images are processed. A certain threshold value is set for imputted images, such as the one shown in FIG. 12, so that the images are converted to binary images at 24 by treating fuzzy regions of the images. Then, the images are subjected to edge treatment, and the lengths of all the minuscule or micro cracks in the images are determined and written in numerals as indicated at 25. Data 26 obtained by writing the lengths of minuscule or micro cracks in numbers is statistically processed by a processor 27 which may be a personal computer, to obtain from samplings the length of the greatest crack existing at the surface of a zone to be inspected. Thereafter, the life expectancy is estimated based on the value of the length of the greatest crack, and the estimate is outputted to a cathode ray tube visual display unit 28 for visual inspection.

Figure 14:
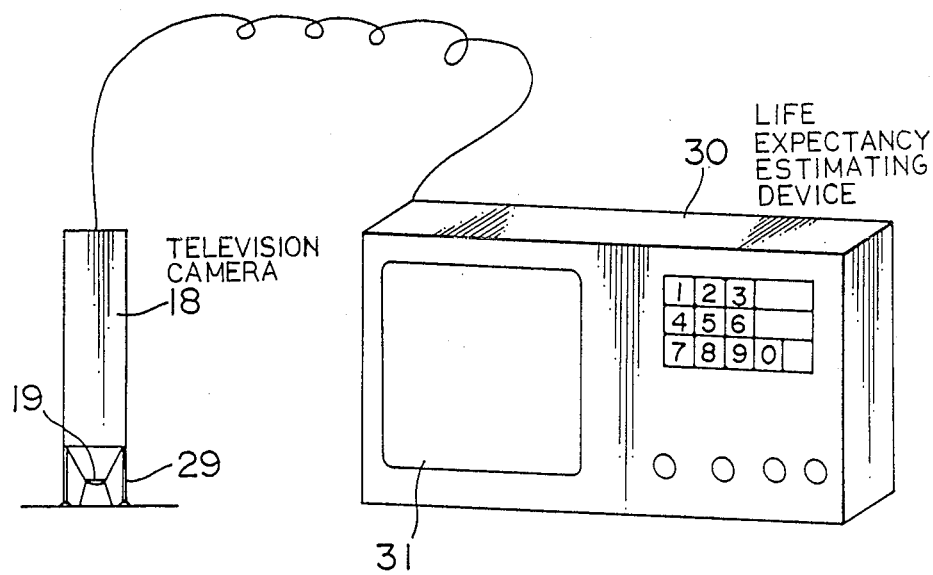
FIGS. 14 and 15 are views of the apparatus comprising other embodiments of the invention.

In the apparatus shown in FIG. 14, a compact size can be obtained in the detecting means by using a solid state image forming element 18 with a television camera provided with a magnifying lens 19. For processing signals inputted from the detecting means 29, life expectancy estimating device 30 of compact size is provided which includes a group of microprocessors and an indicating section 31. By using the detecting means 18 of the aforesaid construction, the operator is able to obtain samplings of damage located in arbitrarily selected positions while monitoring the inputted images displayed by the indicating section 31.

Figure 15:
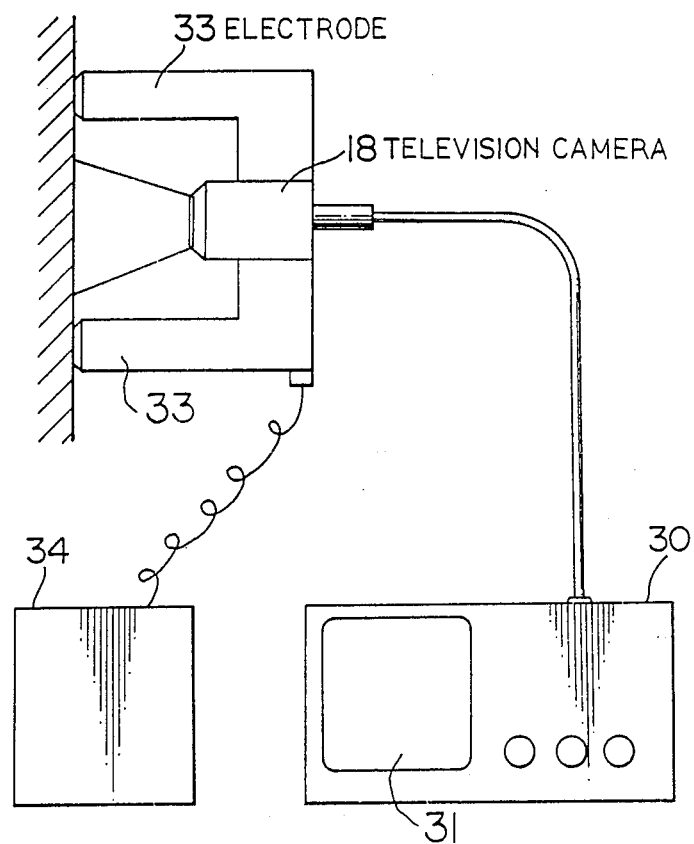

In the apparatus shown in FIG. 15, the detecting means 18 is combined with magnetic flaw detecting means 33 and 34. When this apparatus is used, the surface of a zone to be inspected is magnetized. If there is a flaw at the surface, then the flaw blocks the magnetic flux and the magnetic flux leaks in the position in which the flaw is present, forming a small magnetic pole therein. By applying minuscule iron powder to the flaw, it is possible to form a collection of iron powder which is attracted to the magnetic pole. To facilitate observation of the pattern of the collection of iron powder on the surface of the zone to be inspected, the iron powder used is coated with a fluorescent dye and ultraviolet irradiation is relied on in performing the inspection.

More specifically, when the apparatus shown in FIG. 15 is used, the zone to be inspected is sprayed with a solution of phosphor-containing iron powder and magnetized by means of the power source 34 and the electrode 33. The detecting means 18 of the aforesaid construction is connected to the electrode 34, and a fluorescent lamp is used as a light source to irradiate the zone to be inspected. The use of the apparatus shown in FIG. 15 enables the study of the distribution of minuscule or micro cracks to be performed with increased ease.

From the foregoing, it will be appreciated that the invention enables the life expectancy of structural members of machinery to be estimated based on microscopic damage suffered by the structural members at initial stages of their life. Thus, the invention makes it possible to avoid any accident which might otherwise occur and to ensure that the plant can be operated without any danger.

What is claimed is:

1. A method of estimating a life expectancy of a mechanical structure to which a number of repeated loads is applied, said structure being made of a material and having a surface, comprising the steps of:

experimentally determining a relationship between a length of a maximum length microcrack of microcracks formed in the surface of the material and a life ratio of the material, wherein said life ratio represents a number of repeated loads applied to the material of the structure to an average number of repeated loads applied to the material of the structure when rupture occurs;

estimating a length of a maximum length microcrack within a plurality of microcracks formed in the surface of the material of the structure including detecting a number of lengths of maximum length microcracks, one of said number of lengths from each of a plurality of sampling areas of said structure's surface, and estimating said length of a maximum length microcrack by an extreme value statistical process from said number of lengths of maximum length microcracks;

estimating a life expectancy of the structure by calculating a current life ratio from said estimated length of a maximum length microcrack based on said relationship.

2. An apparatus for estimating a life expectancy of a mechanical structure to which a number of repeated loads is applied, said mechanical structure being made of a material and having a surface, comprising:

means for detecting a length dimension of cracks formed in the surface of the structure within a zone area of the surface of the structure, said means for detecting including means for detecting and producing data indicating a length dimension of cracks in each of a plurality of sampling area located within said zone area;

means receiving said crack length dimension data for determining and producing data representative of a length of a greatest length crack from within each of said sampling areas;

means receiving said greatest length crack data from within each of said sampling areas for statistically processing said greatest length crack data to form a distribution of lengths of said greatest length crack data for said zone area, and further for statistically estimating and producing a signal indicating a statistically estimated length of a greatest length crack within said zone area;

means receiving said statistically estimated greatest length crack signal for estimating and producing a life expectancy value of the structure from a relationship between a length of a greatest length crack formed in the surface of the structure and a life ratio of the structure, wherein a life ratio represents a number of repeated loads applied to the structure to an average number of loads needed to be applied to the structure for rupture to occur; and means responsive to said life expectancy value for displaying the estimated life expectancy value of the structure.

3. An apparatus as claimed in claim 2, wherein said detecting means includes a television camera for viewing the surface of the structure and a magnifying lens positioned between the television camera and the surface of the structure for magnifying the surface of the structure being viewed by the television camera.

4. An apparatus as claimed in claim 2, further comprising:
said detecting means including a television camera for viewing the surface of the structure for producing video signals representative of cracks formed in the surface of the structure;
image analyzing means for receiving said video signals and converting said video signals into said data indicating a length dimension of the cracks being viewed through said television camera; and
said processing means including means for applying an extreme value statistical process to the distribution of greatest length crack data.

5. An apparatus for estimating a life expectancy of a mechanical structure to which a number of repeated loads is applied, said apparatus comprising:
determining and estimating means for experimentally determining a relationship between a maximum crack length of micro cracks formed in the surface of the structure and a life ratio of the structure, wherein a life ratio represents the number of repeated loads applied to the structure to the number of loads needed to be applied to the structure in order for rupture to occur, and for estimating a life expectancy value of the structure by calculating a current life ratio from the maximum crack length of the micro cracks based on said relationship;
detecting means for detecting a maximum crack length and providing a signal indicating said maximum crack length to said determining and estimating means; and
displaying means for receiving and displaying the estimated life expectancy value of the structure.

6. A method of estimating a life expectancy of a mechanical structure to which a number of repeated loads are applied, said structure being made of a metallic material and having a surface, comprising the steps of;
experimentally determining a relationship between lengths of greatest length minuscule cracks formed in the surface of the material and a life ratio of the material with a specimen of the material, said minuscule cracks having a range in length of 50 microns to 10 millimeters, wherein said life ratio represents a number of repeated loads applied to the specimen to a number of repeated loads applied to the specimen when rupture occurs;
determining a zone area of the structure that is subjected to a higher stress concentration than the remainder of the structure, and measuring a length of a greatest length minuscule crack formed in the surface within said zone; and
estimating the life expectancy of the structure by calculating a current life ratio from said measured length based on said relationship.

7. A method of estimating a life expectancy of a mechanical structure to which a number of repeated loads are applied, said structure being made of a metallic material having a crystal structure and having a surface, comprising the steps of:
experimentally determining a relationship between lengths of greatest length minuscule cracks formed in the surface of the material and a life ratio of the material, each of said minuscule cracks having an initial length of a diameter of a grain of crystal structure, wherein said life ratio represents a number of repeated loads applied to a specimen of the material to an average number of repeated loads applied to the specimen of the material in order for rupture to occur;
statistically estimating a length of a greatest length minuscule crack formed in the surface of the structure by conducting an extreme value statistical process on lengths of greatest length minuscule cracks formed in the surface of the structure within each one of several surface sampling areas of the structure; and
estimating the life expectancy of the structure by calculating a current life ratio from the statistically estimated length based on said relationship.

8. A method of estimating a life expectancy of a mechanical structure to which a number of repeated loads are applied, said structure being made of a metallic material having a crystal structure and having a surface, comprising the steps of:
experimentally determining a relationship between lengths of greatest length minuscule cracks formed in the surface of the material and a life ratio of the material, said minuscule cracks having an initial length of a diameter of a grain of the crystal structure, and wherein said life ratio represents the number of repeated loads applied to the material to the number of repeated loads applied to the material when rupture occurs;
calculating an estimated length of a greatest length minuscule crack formed in the surface of the structure by conducting an extreme value statistical process on lengths of greatest length minuscule cracks each formed within one of several surface sampling areas of the structure; and
estimating the life expectancy of the structure by calculating a current life ratio from the estimated length of the greatest length minuscule crack based on said relationship.

9. A method according to claim 8, wherein said step of experimentally determining a relationship is conducted on a specimen of the material; and
wherein said several surface sampling areas are located on the surface of the structure in a zone that is determined to be subjected to greater stress concentration than the remainder of the structure so that creep and fatigue damage suffered by the structure occurring within said zone is greater than outside of said zone.

10. A method of estimating a life expectancy of a mechanical structure to which a number of repeated loads are applied, said structure being made of a metallic material having a crystal structure and having a surface, comprising steps of:
experimentally determining a relationship between a length of greatest length minuscule cracks having a length of no less than a diameter of a grain of the crystal structure formed in the surface of the material and a life ratio of the material, wherein said life ratio represents a number of repeated loads applied to the material to an average number of repeated loads applied to the material when a rupture occurs;
calculating a length of a greatest length minuscule crack by conducting an extreme value statistical process on measured lengths of greatest length minuscule cracks formed in each of several surface sampling areas of the structure, the measured lengths being detected by using video magnifying means for forming a magnified image of the respective surface sampling areas, and image analyzing processor means for converting the image thus formed into signals representing the measured lengths within the imaged area; and estimating the life expectancy of the structure by calculating a current life ratio from the calculated length of the greatest length minuscule crack based on said relationship.

11. A method of determining a degree of damage to a mechanical structure subjected to repeated loading, said mechanical structure having a material, and said material having a crystal structure and a surface, comprising the steps of:

experimentally determining a relationship between lengths of greatest length minuscule cracks formed in the surface of the material and having a range in size of between no less than a diameter dimension of a grain of the crystal structure and 10 millimeters and a life ratio of the structure, wherein said life ration represents a number of repeated loads applied to the material to a number of repeated loads applied to the material when rupture occurs;

estimating a length of a greatest length minuscule crack of all minuscule cracks formed in the surface of the material of the structure including conducting an extreme value statistical process calculating step on respective lengths of greatest length minuscule cracks formed in each of several sampling areas on the surface of the structure, and further locating said sampling areas to correspond with areas of high stress concentration; and estimating a life expectancy of the structure by calculating a current life ratio from the estimated length of the greatest length minuscule crack based on said relationship.

12. The method according to claim 11, wherein said step of experimentally determining a relationship includes determining that a logarithm of twice the length of greatest length minuscule cracks is linearly related to the life ratio of the material.

13. The method according to claim 11, wherein said step of experimentarlly determining a relationship includes conducting experimental tests on a specimen of the material to determine the relationship between lengths of greatest length minuscule cracks formed in the surface of the specimen and a life ratio of the material wherein the life ratio represents the number of repeated loads applied to the material of an specimen to the average number of repeated loads applied to the specimen when rupture occurs.

* * * * *